United States Patent
Schaub et al.

(10) Patent No.: US 10,774,024 B2
(45) Date of Patent: Sep. 15, 2020

(54) PROCESS FOR PREPARING AN UNSATURATED CARBOXYLIC ACID SALT

(71) Applicant: BASF SE, Ludwigshafen am Rhein (DE)

(72) Inventors: Thomas Schaub, Ludwigshafen (DE); Rocco Paciello, Ludwigshafen (DE); Nuria Huguet Subiela, Ludwigshafen (DE); Oliver Trapp, Munich (DE); Simone Manzini, Vercelli (IT)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 16/090,731

(22) PCT Filed: Apr. 4, 2017

(86) PCT No.: PCT/EP2017/057953
§ 371 (c)(1),
(2) Date: Oct. 2, 2018

(87) PCT Pub. No.: WO2017/178282
PCT Pub. Date: Oct. 19, 2017

(65) Prior Publication Data
US 2019/0112251 A1     Apr. 18, 2019

(30) Foreign Application Priority Data

Apr. 11, 2016 (EP) .................... 16164658

(51) Int. Cl.
| | | |
|---|---|---|
| C07C 51/15 | (2006.01) | |
| B01J 31/12 | (2006.01) | |
| B01J 31/18 | (2006.01) | |
| C07C 51/44 | (2006.01) | |
| C07C 57/04 | (2006.01) | |

(52) U.S. Cl.
CPC ........... C07C 51/15 (2013.01); B01J 31/12 (2013.01); B01J 31/189 (2013.01); B01J 2531/824 (2013.01); B01J 2531/847 (2013.01); C07C 51/44 (2013.01); C07C 57/04 (2013.01)

(58) Field of Classification Search
USPC ......................................................... 562/546
See application file for complete search history.

(56) References Cited

U.S. PATENT DOCUMENTS 4,792,620 A * 12/1988 Paulik .................. B01J 31/0231
560/232

FOREIGN PATENT DOCUMENTS

| DE | 968 903 C | 4/1958 |
|---|---|---|
| WO | WO 2011/107559 A2 | 9/2011 |
| WO | WO 2013/098772 A1 | 7/2013 |
| WO | WO 2015/173276 A1 | 11/2015 |
| WO | WO 2015/173277 A1 | 11/2015 |

OTHER PUBLICATIONS

Doherty et al (Journal of Organometallic Chemistry;2001, 640, pp. 182-196.*
International Search Report dated Jun. 12, 2017, in PCT/EP2017/057953 filed Apr. 4, 2017.

* cited by examiner

*Primary Examiner* — Ana Z Muresan
(74) *Attorney, Agent, or Firm* — Oblon, McClelland, Maier & Neustadt, L.L.P.

(57) ABSTRACT

The present invention relates to a catalytic process for preparing an α,β-ethylenically unsaturated carboxylic acid salt, comprising contacting an alkene and carbon dioxide with a carboxylation catalyst being a transition metal complex, an alkoxide, and an organic solvent, to obtain an α,β-ethylenically unsaturated carboxylic acid salt, the organic solvent being incompletely miscible with water at a pressure of 1 bar at at least one temperature T and selected from amides and ureas, T being a temperature in the range from 10° C. to 90° C.

13 Claims, No Drawings

PROCESS FOR PREPARING AN UNSATURATED CARBOXYLIC ACID SALT

The present invention relates to a catalytic process for preparing an α,β-ethylenically unsaturated carboxylic acid salt from an alkene, carbon dioxide, and an alkoxide. α,β-ethylenically unsaturated carboxylic acids, in particular acrylic acid and derivatives thereof are important industrial chemicals and monomer units for producing water-absorbing resins, i.e. superabsorbents.

The direct addition of $CO_2$ onto ethene to give acrylic acid is industrially unattractive due to thermodynamic limitations ($\Delta G=42.7$ kJ/mol at 298 K) and the unfavorable equilibrium, which at room temperature is virtually completely to the side of the reactants ($K_{298}=7\times10^{-7}$). On the other hand, the formation of sodium acrylate and water from $CO_2$, ethene and sodium hydroxide is thermodynamically favored ($\Delta G=-56.2$ kJ/mol at 298 K, $K_{298}=7.1\times10^{9}$). However, the nucleophilic base sodium hydroxide is immediately reacting with $CO_2$ to form sodium carbonate or sodium bicarbonate and hence consumed by a chemical side reaction that does not provide the desired product. Even if less nucleophilic bases are used, the acrylate formation is kinetically inhibited and therefore requires a homogeneous or heterogeneous carboxylation catalyst.

The stoichiometric coupling of $CO_2$ and ethene at homogeneous Nickel complexes has been known since more than 30 years (Hoberg et al., J. Organomet. Chem. 1983, C51). The formation of nickelalactones as intermediates has been discussed, e.g. by Walther et al. (Chem. Commun. 2006, 23, 2510-2512). These do not spontaneously decompose by β-hydride elimination, as according to Walther's initial theory. Many nickelalactones are particularly stable and obtained in the form of solids by stoichiometric coupling of CO2 and ethene (J. Organomet. Chem. 1983, C51; J. Organomet. Chem. 1982, 236, C28; Angew. Chem. Int. Ed. Engl. 1987, 26, 771). Some nickelalactones may even be isolated at room temperature in the form of stable solids (J. Organomet. Chem. 1982, 236, C28).

Nickelalactones are hydrolyzed by mineral acids to yield a saturated carboxylic acid rather than an α,β-ethylenically unsaturated carboxylic acid. Buntine et al. (Organometallics 2007, 26, 6784) and Walther et al. (Eur. J. Inorg. Chem. 2007, 2257) suggest that the initially postulated formation of acrylic acid by β-hydride elimination is energetically unfavored. This also explains for the stability of many nickelalactones. The β-hydride elimination postulated by Walther et al. and the equilibrium between nickelalactone and π-complex has never been realized experimentally.

WO 2011/107559 describes a process for preparing an alkali metal or alkaline earth metal salt of an α,β-ethylenically unsaturated carboxylic acid, wherein a) an alkene, $CO_2$ and a carboxylation catalyst are converted to an alkene/$CO_2$/carboxylation catalyst adduct, b) the adduct is decomposed to release the carboxylation catalyst with an auxiliary base to give the auxiliary base salt of the α,β-ethylenically unsaturated carboxylic acid, c) the auxiliary base salt of the α,β-ethylenically unsaturated carboxylic acid is reacted to release the auxiliary base with an alkali metal or alkaline earth metal base to give the alkali metal or alkaline earth metal salt of the α,β-ethylenically unsaturated carboxylic acid. The intermediate adduct is cleaved by means of an auxiliary base, for example a tertiary amine, in order to prepare, in a first step, the ammonium salt of the α,β-ethylenically unsaturated carboxylic acid, which overcomes the fundamental thermodynamic limitation. In a second step, the ammonium cation is exchanged for sodium, for example by treatment with aqueous sodium hydroxide solution. The auxiliary base salt formed in the first step is separated from the reaction medium, e.g., by liquid-liquid phase separation.

Limbach et al. (WO 2013/098772, Chem. Eur. J. 2012, 18, 14017-14025) described a catalytic process for preparing an alkali metal or alkaline earth metal salt of an α,β-ethylenically unsaturated carboxylic acid, wherein a) a transition metal-alkene complex is reacted with $CO_2$ to give a metallalactone, b) the metallalactone is reacted with a base to give an adduct of the alkali metal or alkaline earth metal salt of the α,β-ethylenically unsaturated carboxylic acid with the transition metal complex, the base being selected from alkali metal or alkaline earth metal hydroxides and alkali metal or alkaline earth metal superbases, and c) the adduct is reacted with an alkene to release the alkali metal or alkaline earth metal salt of the α,β-ethylenically unsaturated carboxylic acid and regenerate the transition metal-alkene complex. In step c), the transition metal-alkene complex is regenerated and is available again for step a). This completes the catalytic cycle. According to the teaching of WO 2013/098772, the base is added separately from the addition of the $CO_2$ in order to prevent a direct reaction of the base with the $CO_2$. In other words, the process requires separation of the times and/or sites of addition of the alkene and $CO_2$ reactants on the one hand and the base reactant on the other hand (page 16 of WO 2013/098772). Dividing the catalytic cycle into two halves: a $CO_2$-rich regime, and a $CO_2$-poor regime is also suggested in Chem. Eur. J. 2012, 18, 14017-14025. As stated at page 14021, it is avoided to expose the reaction mixture to both, alkoxides and carbon dioxide at the same time. It is presumed that the alkoxides would irreversibly form fairly stable carbonic acid half esters with $CO_2$. Accordingly, sodium acrylate was obtained in WO 2013/098772 at an overall yield of 1020% (2.55 mmol) based on the Nickel (0.25 mmol) only after 18 cycles of subsequent treatment of the reaction mixture with $CO_2$ (in a first step) and then with NaOtBu (in a second step). Such a process requires considerable effort, in particular in terms of energy and time, because each cycle includes increasing and decreasing $CO_2$ partial pressure, increasing and decreasing ethene partial pressure, and adding NaOtBu at decreased gas pressure.

Recently, the direct transition metal-catalyzed carboxylation of alkenes with $CO_2$ has been described. It is carried out in the presence of phenoxides, and in particular in the presence of specific fluorine substituted phenoxides or alkyl substituted phenoxides (Chem. Eur. J. 2014, 20, 16858-16862, WO 2015/173276, WO 2015/173277). Catalytic turnover was achieved under simultaneous presence of high $CO_2$ partial pressure and phenoxide base. Maximum turnover was achieved with 2-fluoro phenoxides, 3-fluoro phenoxides, 2,6-dialkyl phenoxides, and 2,4,6-trialkyl phenoxides.

The use of these specific phenoxide bases provided great progress towards the industrial application of the catalytic formation of α,β-ethylenically unsaturated carboxylic acid salts form ethene, carbon dioxide and bases. Nevertheless, the industrial application of the processes described in Chem. Eur. J. 2014, 20, 16858-16862, WO 2015/173276, WO 2015/173277 is challenging. Organofluorine compounds (e.g. fluoro substituted phenoxide bases and the corresponding phenols) are potentially harmful pollutants even when only small amounts are emitted from production sites. It has further been found that dialkyl- or trialkylsubstituted phenoxides and the corresponding phenols, do make the work-up of the crude carboxylation product more difficult (*Eur. J. Org. Chem.* 2015, 32, 7122-7130). In particular, liquid-liquid phase separation was found to be complicated because stable emulsions were formed when such phenoxides or phenols were present. The separation of the main product ($\alpha,\beta$-ethylenically unsaturated carboxylic acid salt) from the phenolic byproduct is further complicated as both, the main and the byproduct, possess similar solubility in polar and apolar solvents. It is further difficult to distill of phenol byproducts because of their low volatility. Carrying out these prior art transition metal-catalyzed carboxylation processes on an industrial scale would thus require substantial effort for avoiding any emission of base or for the separation of the $\alpha,\beta$-ethylenically unsaturated carboxylic acid salt from the crude reaction product.

The problem of the present invention is thus the provision of a catalytic process for preparing $\alpha,\beta$-ethylenically unsaturated carboxylic acid derivatives from $CO_2$ and an alkene on an industrial scale more efficiently, in particular to overcome the risk of emitting potentially harmful compounds and to avoid any additional effort for obtaining a sufficiently pure $\alpha,\beta$-ethylenically unsaturated carboxylic acid salt.

The problem is solved by a catalytic process for preparing an $\alpha,\beta$-ethylenically unsaturated carboxylic acid salt, comprising contacting an alkene and carbon dioxide with a carboxylation catalyst being a transition metal complex, an alkoxide, and an organic solvent, to obtain an $\alpha,\beta$-ethylenically unsaturated carboxylic acid salt, the organic solvent being incompletely miscible with water at a pressure of 1 bar at at least one temperature T and selected from amides and ureas, T being a temperature in the range from 10° C. to 90° C.

According to the invention, the organic solvent is incompletely miscible at at least one temperature T in the range from 10° C. to 90° C. The organic solvent can, for example, be incompletely miscible with water only at a single temperature (or small temperature range) within the range from 10° C. to 90° C., or, be incompletely miscible with water in most or all of the range from 10° C. to 90° C., or, be incompletely miscible with water in temperature ranges that overlap with the upper or lower end of the range from 10° C. to 90° C. In each of these examples, the condition of incomplete miscibility with water at at least one temperature T in the range from 10° C. to 90° C. is fulfilled.

A skilled person can, for example, test the miscibility of an organic solvent with water by slowly adding water to the organic solvent. The presence of a stable second liquid phase, i.e., a second liquid phase that does not disappear when stirring is continued, indicates incomplete miscibility. A second liquid phase may, for example, occur when excess organic solvent is present or when excess water is present or when similar amounts of organic solvent and water are present. Such a test can easily be carried out at many temperatures in order to assess the miscibility of an organic solvent with water within the range from 10° C. to 90° C.

The $\alpha,\beta$-ethylenically unsaturated carboxylic acid salt is comprised by a crude reaction product that is obtained when the alkene and carbon dioxide are contacted with the carboxylation catalyst, the alkoxide, and the organic solvent.

The catalytic process according to the invention may comprise additional steps, e.g. steps in which the crude reaction product is treated. Any reference to "step a)" provided herein relates to contacting the alkene and carbon dioxide with the carboxylation catalyst, the alkoxide, and the organic solvent, to obtain the $\alpha,\beta$-ethylenically unsaturated carboxylic acid salt, as specified herein.

It was surprising that significant catalytic turnover was achieved when the above specified hydrophobic amide or urea solvent was used together with the alkoxide base. A range of different solvents and bases had been tested in earlier attempts for developing a process for the direct catalytic carboxylation of alkenes with $CO_2$ in the presence of base. As regards to the solvent, maximum turnover was reached in volatile ethers such as THF, in anisole, and in toluene, whereas turnover numbers were much smaller in the amide DMF (end of left column at page 16859 and Table 1 in Chem. Eur. J. 2014, 20; Tables 4 and 9 in WO 2015/173276). As regards to the base, turnover numbers reached with alkoxide bases (WO 2015/173276, examples 3a, 3b) were even in the previously preferred solvent THF in general much smaller than turnover numbers reached with the above described specific fluorinated or alkylated phenoxide bases.

It was so far assumed that solvents such as N-methylpyrrolidone or N-methylcaprolactam could serve as constituents of polar solvents for the work-up of the crude reaction product of the carboxylation reaction (page 24, line 8 in WO 2015/173276) but not as solvents for the catalytic reaction itself.

Using the catalytic process according to the invention, $\alpha,\beta$-ethylenically unsaturated carboxylic acid derivatives can be produced from $CO_2$ and an alkene on an industrial scale more efficiently. A significant catalytic turnover, i.e. the provision of the $\alpha,\beta$-ethylenically unsaturated carboxylic acid salt at molar excess based on the transition metal, is achieved in a single stage. There is no risk of emitting potentially harmful compounds and any additional effort for obtaining a sufficiently pure $\alpha,\beta$-ethylenically unsaturated carboxylic acid salt is avoided. Fluoro substituted compounds are not used and can therefore not be emitted. The emission of alcohol byproducts is in general considered to be less harmful than the emission of fluoro substituted phenol byproducts. The above-mentioned phase separation problems that are caused by phenolic compounds in prior art processes are avoided because phenolic compounds are not used. It is important to note that it is the specific composition of the crude reaction product that facilitates subsequent processing steps. Very high accumulated multi stage catalytic turnover can easily be reached even at relatively low single stage catalytic turnover by recycling (and regenerating) of the desired parts of the processed crude reaction product into the reactor.

The crude reaction product can thus, for example, be processed further in a separation process that comprises a phase separation step (which may, for example be carried out after a polar solvent has been added), and a partial evaporation step, e.g., distilling off at least part of the alcohol (byproduct). The phase separation and the partial evaporation steps may be carried out in any order.

A specific organic solvent is used in the processes according to the invention. This organic solvent is incompletely miscible with water at a pressure of 1 bar at at least one temperature T and selected from amides and ureas. T is a temperature in the range from 10° C. to 90° C. It is assumed that this specific organic solvent helps to solubilize the $CO_2$ as well as intermediates formed in the carboxylation reaction and therefore increases the turnover number.

The solvent may be an amide or a urea or contain at least one amide and at least one one urea substructure. It may be a monomer or a linear or cyclic oligomer, e.g., dimer, trimer, or tetramer, comprising multiple, e.g. two, three, or four amide or urea subunits. The term amides refers to carboxamides and sulfonamides; preferred amides are carboxamides. The term ureas refers to carbamides and sulfamides; preferred ureas are carbamides.

The organic solvent can, for example, be selected from amides and ureas of which at most 10% by weight, preferably at most 8% by weight, more preferably at most 6% by weight, most preferably at most 4% by weight, in particular at most 2% by weight are soluble in water at a pressure of 1 bar at at least one temperature T, based on the total weight of water and solvent. The solubility of the organic solvent in water determines the amount of organic solvent that is dissolved in an aqueous phase used for extracting α,β-ethylenically unsaturated carboxylic acid salt from the crude reaction product. The loss of solvent via the aqueous phase (the first liquid phase), is thus kept at a minimum. This facilitates the recycling of the solvent into the carboxylation reaction and the further purification of the α,β-ethylenically unsaturated carboxylic acid salt from the first liquid phase.

The organic solvent is preferably aprotic. Aprotic means that the solvent molecule does not contain a heteroatom-bound hydrogen atom, e.g. a nitrogen-bound hydrogen atom or an oxygen-bound hydrogen atom. This is advantageous as the absence of heteroatom-bound hydrogen atoms tends to reduce the miscibility with water and to suppress undesired side reactions even further. Most preferably, every hydrogen atom comprised by the organic solvent molecule is bound to a carbon atom.

Preferably, the amide, e.g. carboxamide, or urea, e.g. carbamide, is linear or cyclic, comprises at least 5 carbon atoms, e.g., 5 to 20 carbon atoms, preferably 6 to 18 carbon atoms, most preferably 7 to 16 carbon atoms, all carbon atoms other than the carbonyl carbon atom being saturated, and comprises no nitrogen-bound hydrogen atom.

The organic solvent is, for example, an N,N-disubstituted formamide, an N,N-disubstituted acetamide, an N-substituted 2-pyrrolidone, or an 1,3-disubstituted 2-imidazolidinone. The substituents are preferably independently selected from linear or branched $C_1$-$C_{16}$-alkyl, and $C_3$-$C_9$-cycloalkyl.

Specific examples of organic solvents are N-Methylpyrrolidone, N-Ethylpyrrolidone, 1,3-Dimethyl-2-imidazolidinone, N-Cyclohexylpyrrolidone, N,N-Dibutylformamide, N,N-Diisobutylformamide, N,N-Dihexylformamide, N,N-Dibutylacetamide, N,N-Dihexylacetamide, N-Cyclohexylpyrollidone, and N-Decylpyrollidone. N,N-Dibutylformamide and N-Cyclohexylpyrrolidone are particularly preferred organic solvents. The most preferred organic solvent is N,N-Dibutylformamide.

The organic solvent used in the process according to the invention may, for example, be an amide, for example, a formamide, wherein no hydrogen atom is bound to a nitrogen atom, wherein every carbon atom other than the carbonyl carbon atom comprised by the amide group is saturated, and which has the general formula

$C_aH_bN_1O_1$ wherein a is an integer from 5 to 20, e.g., 6 to 18, preferably 7 to 16, and
b is an integer from 2a−5 to 2a+1,
or a urea wherein no hydrogen atom is bound to a nitrogen atom, wherein every carbon atom other than the carbonyl carbon atom comprised by the amide group is saturated, and which has the general formula

$C_cH_dN_2O_1$ wherein c is an integer from 5 to 20, e.g., 6 to 18, preferably 7 to 16, and
d is an integer from 2c−4 to 2c+2.

Any alkoxide may be used in the process according to the invention. Preferably, the alkoxide has a secondary or tertiary carbon atom directly bound to a [O⁻] group. Although primary alkoxides may be used, the process is in general more efficient when secondary or tertiary alkoxides are used. According to the invention, the alkoxide is thus preferably an alkoxide having a secondary or tertiary carbon atom directly bound to a [O⁻] group. It is assumed that any undesired direct reaction of the alkoxide with $CO_2$ and in particular the undesired formation of half esters is more efficiently suppressed when the residue bound to the [O⁻] group is sterically demanding. In general, tertiary residues are sterically more demanding than secondary residues. The alkoxide is thus preferably tertiary. This means that the alkoxide is preferably an alkoxide having a tertiary carbon atom directly bound to the [O⁻] group.

The alkoxide that has a secondary or tertiary carbon atom directly bound to a [O⁻] group refers to a compound comprising subunits of the following general formula (I)

⁻O—R  (1)

wherein R is a hydrocarbyl residue which comprises a carbon atom that is bound to the oxygen shown in general formula (I), and
one hydrogen atom that is bound to this carbon atom and two carbon atoms that are bound to this carbon atom,
or
three carbon atoms that are bound to this carbon atom.

Accordingly, the expression "alkoxide having a tertiary carbon atom directly bound to a [O⁻] group" refers to a compound comprising at least one subunit, preferably one subunit, of general formula (I) wherein R is a hydrocarbyl residue which comprises a carbon atom that is bound to the oxygen shown in general formula (I), and three carbon atoms that are bound to this carbon atom.

The hydrocarbyl residue R may be acyclic, cyclic or comprise cyclic substructures. R is preferably acyclic.

The hydrocarbyl residue R may be saturated or unsaturated. Hydrocarbyl residues R that are saturated do only comprise single bonds, whereas hydrocarbyl residues R that are unsaturated do comprise at least one double bond. The hydrocarbyl residue R is preferably saturated.

Any hydrogen atom comprised by R may, for example, be substituted by one or multiple non-interfering substituents. A non-interfering substituent is a substituent that is inert under the conditions of the processes according to the invention, i.e. a substituent that does not react with any compound or intermediate being in contact with the alkoxide or with the conjugate acid of the alkoxide in the processes according to the invention. Suitable substituents include, for example, O—$C_1$-$C_{16}$-alkyl. R is preferably unsubstituted which means that R consists of hydrogen and carbon atoms.

Preferably, the alkoxide having a secondary or tertiary carbon atom directly bound to a [O⁻] group comprises subunits of the following general formula (II)

—O—CR¹(R²)₂  (II)

wherein
$R^1$ is H or $R^2$, and
each $R^2$ is independently selected from $C_1$-$C_{16}$-hydrocarbyl or any two or three $R^2$ together with the secondary or tertiary carbon atom to which they are bonded are one or multiple 3- to 8-membered carbocycles.

Each $R^2$ is preferably independently selected from $C_1$-$C_{16}$-alkyl, $C_3$-$C_{16}$-cycloalkyl, and $C_6$-$C_{14}$-aryl, most preferably from $C_1$-$C_{10}$-alkyl, and $C_3$-$C_{10}$-cycloalkyl.

Most preferably, the alkoxide having a secondary or tertiary carbon atom directly bound to a [O⁻] group comprises subunits selected from ⁻O-tert-butyl, ⁻O-sec-propyl, ⁻O-sec-butyl, ⁻O-cyclopropyl, and ⁻O-((1-methyl)-cyclopropyl), ⁻O-cyclohexyl, and ⁻O-((1-methyl)-cyclohexl).

A preferred secondary alkoxide is iso-propoxide.

A preferred tertiary alkoxide is tert-butoxide.

The alkoxide is, for example, selected from alkali metal alkoxides and alkaline earth metal alkoxides. Alkali metal and in particular sodium alkoxides are preferred.

Preferred alkoxides are sodium iso-propoxide and sodium tert-butoxide. The most preferred alkoxide is sodium tert-butoxide. The alkoxide can, for example, be added in solid form or as a solution.

The carboxylation catalyst is a transition metal complex.

The term "transition metal complex" used herein comprises, in a generic manner, all transition metal complexes through which the catalytic cycle is supposed to pass, i.e. transition metal-alkene complexes, metallalactones and adducts wherein the α,β-ethylenically unsaturated carboxylic acid salt coordinates to the transition metal.

In general, the transition metal complex comprises, as the active metal, at least one element of groups 4 (preferably Ti, Zr), 6 (preferably Cr, Mo, W), 7 (preferably Re), 8 (preferably Fe, Ru), 9 (preferably Co, Rh) and 10 (preferably Ni, Pd, Pt) of the Periodic Table of the Elements. Preference is given to nickel and palladium. Most preferably, the transition metal complex is a palladium complex.

In a particularly preferred process according to the invention, the carboxylation catalyst a palladium complex, the alkoxide is selected from sodium iso-propoxide and sodium tert-butoxide, and the organic solvent is selected from N,N-Dibutylformamide and N-Cyclohexylpyrrolidone, in particular, N,N-Dibutylformamide.

The role of the active metal consists in the activation of $CO_2$ and the alkene in order to form a C—C bond between $CO_2$ and the alkene. It is assumed that a metallalactone is formed within the catalytic cycle from the alkene, carbon dioxide and the transition metal complex. The expression "metallalactone" denotes, according to the exchange nomenclature ("a" nomenclature), a lactone (γ-lactone) in which a carbon atom has been exchanged for a metal atom. The expression "metallalactone" should be interpreted broadly and may comprise compounds with structures similar to the well-known five-membered Hoberg complex, or related compounds of oligomeric or polymeric structure. The expression shall comprise isolable compounds and (unstable) intermediates.

The metallalactone can be illustrated by the following general formula

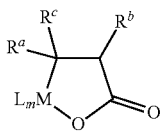

in which

M is the transition metal,

L is a ligand, m is 1 or 2, and $R^a$, $R^b$ and $R^c$ are each independently hydrogen, $C_{1-12}$-alkyl, $C_{2-12}$-alkenyl, or $R^a$ and $R^b$ together with the carbon atoms to which they are bonded are a saturated or mono- or diethylenically unsaturated, 5- to 8-membered carbocycle.

It is assumed that the alkoxide deprotonates the metallalactone at the α-carbon atom.

Preferably, the transition metal complex comprises a ligand that coordinates to the transition metal via at least one ligand atom selected from P, N, O, and C. The ligand preferably comprises at least one phosphorus atom which coordinates to the transition metal. The ligand may be monodentate or polydentate, for example bidentate. In general, two monodentate ligands or one bidentate ligand coordinate to the transition metal. Preferred ligands comprise bulky substituents, as for example the tert-butyl groups in 1,2-bis(di-tert-butylphosphino)ethane or the cyclohexyl groups in 1,2-bis(dicyclohexylphosphino)ethane or 1,2-bis(didodecenylphosphino)ethane, 1,2-bis(diisopropylphosphino)ethane, 1,2-Bis(di-t-butylmethylphosphino)benzene and 1,2-bis(dicyclopentylphosphino)ethane.

The polydentate, e.g. bidentate, ligand may coordinate to the transition metal to form a four-, five-, six-, seven-, or eight-membered ring, i.e. the transition metal, the atoms which coordinate to the transition metal, e.g., nickel or palladium, and the atoms of the shortest chain which connects the atoms coordinating to the transition metal, e.g., nickel or palladium, together form a four-, five-, six-, seven-, or eight-membered ring. Ligands that coordinate to the transition metal, e.g., nickel or palladium, to form a five-, six-, or seven-membered ring are preferred.

Alternatively, the atoms which coordinate to the transition metal may be directly bound to carbon atoms of two cyclopentadienyl ligands bound to a second metal, e.g., iron.

At least one residue is preferably bound via a secondary, tertiary or aromatic, e.g., via a secondary or tertiary carbon atom to a transition metal coordinating phosphorus atom. More particularly, at least two residues are preferably bound to the phosphorus atom via a secondary, tertiary or aromatic, e.g., via a secondary or tertiary carbon atom.

Suitable residues bound to the phosphorus atom via a secondary or tertiary carbon atom are, for example, adamantyl, tert-butyl, sec-butyl, isopropyl, cyclohexyl, cyclopentyl, phenyl, tolyl, xylyl, mesityl, naphthyl, fluorenyl, or anthracenyl, especially tert-butyl, isopropyl, cyclohexyl, or cyclopentyl. At least one residue is preferably bound via a primary carbon atom to a transition metal coordinating phosphorous atom.

Suitable residues bound to the phosphorus atom via a primary carbon atom are, for example, methyl, 1-ethyl, 1-propyl, 1-butyl.

Suitable monodentate ligands have, for example, the formula (IIe)

$$PR^{4a}R^{4b}R^{4c} \qquad (IIe)$$

wherein $R^{4a}$, $R^{4b}$, and $R^{4c}$ are independently an unbranched or branched, acyclic or cyclic, aliphatic, araliphatic or aromatic residue having 1 to 16 carbon atoms, where individual carbon atoms may independently be replaced by a hetero group selected from the group of —O— and >N—, individual hydrogen atoms may independently be replaced by Cl, Br, I, or F, and two or all three residues may be covalently bound to one another.

$R^{4a}$, $R^{4b}$, and $R^{4c}$ are preferably independently $C_1$-$C_{12}$-alkyl, $C_3$-$C_{12}$-cycloalkyl, or $C_3$-$C_{14}$-aryl, wherein $C_3$-$C_{12}$-cycloalkyl and $C_3$-$C_{14}$-aryl are unsubstituted or substituted with 1, 2, 3, or 4 substituents independently selected from Cl, Br, I, F, $C_1$-$C_8$-alkyl and $C_1$-$C_4$-alkoxy.

$R^{4a}$, $R^{4b}$, and $R^{4c}$ are most preferably independently methyl, ethyl, 1-propyl, 2-propyl, 1-butyl, 2-butyl, tert-butyl, 1-(2-methyl)propyl, 2-(2-methyl)propyl, 1-pentyl, 1-(2-methyl)pentyl, 1-hexyl, 1-(2-ethyl)hexyl, 1-heptyl, 1-(2-propyl)heptyl, 1-octyl, 1-nonyl, 1-decyl, 1-undecyl, 1-dodecyl, adamantyl, cyclopentyl, methylcyclopentyl, cyclohexyl, methylcyclohexyl, cycloheptyl, cyclooctyl, norbornyl, phenyl, napthyl, tolyl, xylyl, chlorophenyl or anisyl.

Examples of suitable ligands of formula (IIe) are trialkylphosphines, i.e. tri-n-propylphosphine, tri-n-butylphosphine, tri-tert-butylphosphine, trioctylphosphine; tricycloalkylphosphines, i.e. tricyclohexylphosphine, tricyclododecylphosphine; triarylphosphines; i.e. triphenylphosphine, tritolylphosphine, tri(methoxyphenyl)phosphine, trinaphthylphosphine, di-(chlorphenyl)-phenylphosphine; and dialkylarylphosphines, i.e. diethylphenylphosphine, dibutylphenylphosphine.

The ligand is preferably a bidentate P,X ligand in which X is selected from the group consisting of P, N, O, and carbene, in particular a bidentate P,P ligand. The P and X atoms are, for example, separated by a bivalent linker that comprises 2 to 4 bridging atoms. The linker is preferably linked to the P atom by a single bond and linked to the X atom by a single bond and comprises 2 to 4 bridging atoms linked by single bonds.

A preferred bidentate P,P ligand meets at least one of the following conditions:

condition 1: the bridging atoms are part of at least one 5- to 7-membered cyclic substructure, condition 2: at least one 5- to 7-membered cyclic substructure is bound to each of the P atoms.

In preferred bidentate P,P ligands, wherein the bridging atoms are part of at least one 5- to 7-membered cyclic substructure, each bridging atom directly linked to a P atom, together with the P atom to which it is linked, is part of a 5- to 7-membered cyclic substructure; or two neighboring bridging atoms are part of a 5- to 7-membered cyclic substructure.

Preferred bidentate P,P ligands are ligands of formula (IIa)

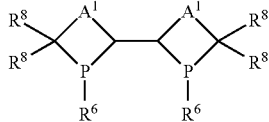

(IIa)

wherein $R^6$ is independently selected from $CHR^7{}_2$, $CR^7{}_3$, $C_3$-$C_{10}$-cycloalkyl, and optionally alkylated aryl having 6 to 18 carbon atoms, $R^7$ is independently selected from $C_1$-$C_4$-alkyl, preferably linear $C_1$-$C_4$-alkyl, $A^1$ together with the carbon atoms to which it is bound and the interjacent phosphorous atom forms a 5- to 7-membered cyclic substructure, and $R^8$ is independently selected from hydrogen, $C_1$-$C_{12}$-alkyl, $C_3$-$C_{12}$-cycloalkyl, $C_3$-$C_{12}$-heterocycloalkyl, $C_6$-$C_{14}$-aryl, $C_6$-$C_{14}$-heteroaryl, $C_1$-$C_{12}$-alkoxy, $C_3$-$C_{12}$-cycloalkoxy, $C_3$-$C_{12}$-heterocycloalkoxy, $C_6$-$C_{14}$-aryloxy, and $C_6$-$C_{14}$-heteroaryloxy.

$A^1$ is preferably selected from —$(CR^8{}_2)_j$— and —$(CR^9=CR^9)_k$— with both $R^9$ being on the same side of the double bond, wherein $R^8$ is independently selected from H, $C_1$-$C_3$-alkyl, and —O—$C_1$-$C_3$-alkyl, $R^9$ is selected from H and $C_1$-$C_3$-alkyl, or at least two $R^9$ constitute a bridge of one of the formulae:

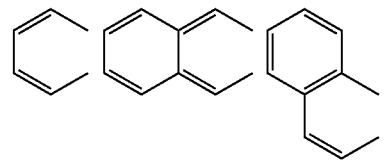

j is 2 or 3, and k is 1 or 2.

$R^6$ is preferably independently selected from $CHR^7{}_2$, $CR^7{}_3$, and $C_3$-$C_8$-cycloalkyl, most preferably $CR^7{}_3$.

$R^7$ is preferably methyl.

$R^8$ is preferably H.

$A_1$ is preferably selected from ethylene, ethenylene, 1,2-phenylene, 1,2-naphthylene, 2,3-naphthylene, and the following formulae:

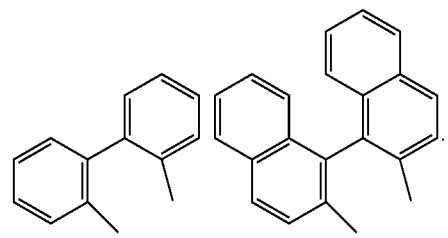

Preferred bidentate P,P ligands are ligands of formula (IIb)

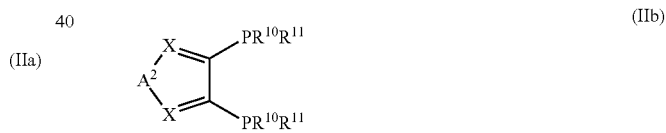

(IIb)

wherein $R^{10}$ is independently selected from linear $C_1$-$C_4$-alkyl, $R^{11}$ is independently selected from $CHR^{10}{}_2$, $CR^{10}{}_3$, $C_3$-$C_{10}$-cycloalkyl, and optionally alkylated aryl having 6 to 18 carbon atoms, X is independently selected from C—H, C—$CH_3$, and N, and $A^2$ together with the moieties X to which it is bound and the interjacent carbon atoms forms a 5- to 7-membered cyclic substructure.

$R^{10}$ is preferably independently selected from $C_1$-$C_6$-alkyl and $C_3$-$C_7$-cycloalkyl and $R^{11}$ is $CR^{10}{}_3$.

$R^{10}$ may, for example, be independently selected from linear $C_1$-$C_4$-alkyl, in particular from linear $C_1$-$C_2$-alkyl.

$R^{11}$ is preferably independently selected from $CHR^{10}{}_2$, $CR^{10}{}_3$, and $C_3$-$C_8$-cycloalkyl.

$A^2$ is preferably a —CH=CH— bridge.

X is preferably CH.

Preferred bidentate P,P ligands are ligands of formula (IIc)

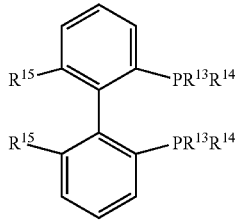

(IIc)

wherein
$R^{13}$ and $R^{14}$ are independently selected from $C_3$-$C_{10}$-cycloalkyl, e.g, $C_5$-$C_7$-cycloalkyl, and
$R^{15}$ is H, O—$C_1$-$C_6$-alkyl, or both $R_{15}$ together constitute a —CH=CH— bridge.
$R^{15}$ is preferably H or $OCH_3$ and most preferably H.

In a particularly preferred bidentate P,P ligand, each of the bridging atoms is unbranched and none of the bridging atoms is part of any cyclic substructure apart from the ring including the transition metal. In a particularly preferred bidentate P,P ligand, the P atoms are separated by a linker that comprises 2 bridging carbon atoms, each P atom being linked to the linker and to two secondary carbon bound residues by single bonds, and the bridging carbon atoms being linked by a single bond. The expression "secondary carbon bound residue" refers to a residue that is bound to the P atom via a secondary carbon atom that is comprised by the residue. Each of the four secondary carbon bound residues may be the same or different and preferably selected from secondary $C_3$-$C_{20}$-hydrocarbyl residues wherein any hydrogen atom comprised by the secondary $C_3$-$C_{20}$-hydrocarbyl residues may be substituted by one or multiple non-interfering substituents. A non-interfering substituent is a substituent that is inert under the conditions of the processes according to the invention, i.e. a substituent that does not react with any compound or intermediate being in contact with the ligand in the processes according to the invention. Suitable non-interfereing substituents include, for example, O—$C_1$-$C_6$-alkyl. The secondary $C_3$-$C_{20}$-hydrocarbyl residues are preferably unsubstituted which means that they consist of hydrogen and carbon atoms. Preferred unsubstituted secondary $C_3$-$C_{20}$-hydrocarbyl residues are 2-propyl, 2-butyl, 2-pentyl, 3-pentyl, cyclopentyl, cyclohexyl, and cycloheptyl. The preferred linker is —$CH_2$—$CH_2$—.

Particularly preferred ligands are bidentate P,P ligands of formula (IId)

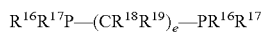

(IId)

wherein
$R^{16}$ and $R^{17}$ are independently an unbranched or branched, acyclic or cyclic, aliphatic residue having 1 to 20 carbon atoms, where individual carbon atoms may independently be replaced by a hetero group selected from the group of —O— and >N—, individual hydrogen atoms may independently be replaced by Cl, or F, and any two residues bound to the same phosphorous atom may be covalently bound to one another,
e is 1, 2, 3, 4, or 5, preferably 2, 3, or 4,
$R^{18}$ is independently selected from H, $C_1$-$C_8$-alkyl, $C_1$-$C_8$-alkoxy, $C_3$-$C_{10}$-cycloalkyl, $C_3$-$C_{10}$-cycloalkoxy, $C_6$-$C_{10}$-aryl, and $C_6$-$C_{10}$-aryloxy, and
$R^{19}$ is independently selected from H, $C_1$-$C_8$-alkyl, $C_3$-$C_{10}$-cycloalkyl, and $C_6$-$C_{10}$-aryl.

Preferably, $(CR^{18}R^{19})_e$ is —$CH_2$—$CH_2$—, —$CH_2$—$CH_2$—$CH_2$—, or —$CH_2$—$CH_2$—$CH_2$—$CH_2$—.
$R^{16}$ and $R^{17}$ are preferably independently $C_1$-$C_{20}$-alkyl, or $C_3$-$C_{20}$-cycloalkyl, wherein $C_1$-$C_{20}$-alkyl is unsubstituted or substituted with 1, 2, 3, or 4 substituents independently selected from Cl, F, and $C_1$-$C_4$-alkoxy and wherein $C_3$-$C_{20}$-cycloalkyl is unsubstituted or substituted with 1, 2, 3, or 4 substituents independently selected from Cl, F, $C_1$-$C_8$-alkyl and $C_1$-$C_4$-alkoxy.

$R^{16}$ and $R^{17}$ are most preferably independently methyl, ethyl, 1-propyl, 2-propyl, 1-butyl, 2-butyl, tert-butyl, 1-(2-methyl)propyl, 1-pentyl, 1-(2-methyl)pentyl, 1-hexyl, 1-(2-ethyl)hexyl, 1-heptyl, 1-(2-propyl)heptyl, 1-octyl, 1-nonyl, 1-decyl, 1-undecyl, 1-dodecyl, adamantyl, cyclopentyl, methylcyclopentyl, cyclohexyl, methylcyclohexyl, cycloheptyl, cyclooctyl, or norbornyl, in particular independently 2-propyl, 2-butyl, tert-butyl, adamantyl, cyclopentyl, methylcyclopentyl, cyclohexyl, methylcyclohexyl, cycloheptyl, cyclooctyl, or norbornyl.

Particularly preferred ligands are bidentate P,P ligands of formula (IId-1)

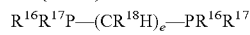

(IId-1)

wherein
$R^{16}$ and $R^{17}$ are each independently an unbranched or branched, acyclic or cyclic aliphatic residue having 1 to 20 carbon atoms,
e is 2, 3, or 4, and
$R^{18}$ is independently selected from H, $C_1$-$C_8$-alkyl, $C_1$-$C_8$-alkoxy, $C_3$-$C_{10}$-cycloalkyl, $C_3$-$C_{10}$-cycloalkoxy, $C_6$-$C_{10}$-aryl, and $C_6$-$C_{10}$-aryloxy, and preferably H.

In particularly preferred processes according to the invention, the ligand is selected from 1,2-bis(dicyclohexylphosphino)ethane, 1,3-bis(dicyclohexylphosphino)propane, 1,4-bis(dicyclohexylphosphino)butane, 1,2-bis(dicyclopentylphosphino)ethane, 1,3-bis(dicyclopentylphosphino)propane, 1,4-bis(dicyclopentylphosphino)butane, 1,2-bis(dicycloheptylphosphino)ethane, 1,3-bis(dicycloheptylphosphino)propane, 1,4-bis(dicycloheptylphosphino)butane, 1,2-bis(diisopropylphosphino)ethane, 1,3-bis(diisopropylphosphino)propane, 1,4-bis(diisopropylphosphino)butane, 1,2-bis(di-sec-butylphosphino)ethane, 1,3-bis(di-sec-butylphosphino)propane, 1,4-bis(di-sec-butyl phosphino)butane, 1,2-bis(dodecylphosphino)ethane, 1,3-bis(dodecylphosphino)propane, 1,4-bis(dodecylphosphino)butane, 1,2-bis(decylphosphino)ethane, 1,3-bis(decylphosphino)propane, 1,4-bis(decylphosphino)butane, 1,2-bis(tetradecylphosphino)ethane, 1,3-bis(tetradecylphosphino)propane, 1,4-bis(tetradecylphosphino)butane, 1,2-bis(hexadecylphosphino)ethane, 1,3-bis(hexadecylphosphino)propane, 1,4-bis(hexadecylphosphino)butane, 1,2-bis(di-tert-butylphosphino)ethane, 1,3-bis(di-tert-butylphosphino)propane, 1,4-bis(di-tert-butylphosphino)butane, and

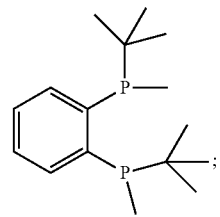 [SMILES: CP(c1ccccc1P(C)C(C)(C)C)C(C)(C)C]

preferably from 1,2-bis(dicyclohexylphosphino)ethane, 1,2-bis(diisopropylphosphino)ethane, 1,2-bis(dodecylphosphino)ethane, 1,2-bis(di-tert-butylphosphino)ethane, 1,2-bis(dicyclopentylphosphino)ethane, and

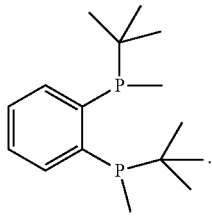 [SMILES: CP(c1ccccc1P(C)C(C)(C)C)C(C)(C)C]

Suitable ligands are, for example, bidentate and multidentate ligands that comprise one or two coordinating phosphorous atoms and an additional carbon atom or hetero atom that is bound to the transition metal. Preferably, a 5-membered ring is formed, when the additional carbon atom or hetero atom binds to the transition metal, as for example with (diphenylphosphino)acetate known from the SHOP-Process or with 2-(dimethylphosphino)-N,N-dimethylethanamine. Specific bidentate ligands are ligands of formula (IIg)

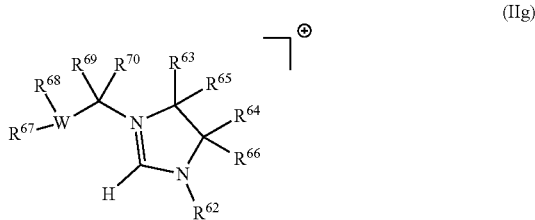

(IIg)

wherein

W is phosphorous (P) or phosphite (P=O), $R^{62}$, is independently an unbranched or branched, acyclic or cyclic, aliphatic, araliphatic or aromatic residue having 1 to 16 carbon atoms, where individual carbon atoms may independently be replaced by a hetero group selected from the group of —O— and >N—, and where individual hydrogen atoms may independently be replaced by Cl or F, $R^{63}$ and $R^{64}$ are independently an unbranched or branched, acyclic or cyclic, aliphatic, araliphatic or aromatic residue having 1 to 16 carbon atoms, where individual carbon atoms may independently be replaced by a hetero group selected from the group of —O— and >N—, individual hydrogen atoms may independently be replaced by Cl, Br, I, or F, and both residues may be covalently bound to one another, $R^{65}$ and $R^{66}$ together are a chemical bond, or as defined for $R^{63}$ and $R^{64}$ $R^{67}$ and $R^{68}$ are as defined for $R^{63}$ and $R^{64}$, and $R^{69}$ and $R^{70}$ are as defined for $R^{63}$ and $R^{64}$.

Preferably $R^{63}$, $R^{64}$, $R^{65}$ and $R^{66}$ are independently hydrogen, $C_1$-$C_{12}$-alkyl, or $C_1$-$C_{14}$-aryl; or $R^{63}$ and $R^{64}$ are independently hydrogen, $C_1$-$C_{12}$-alkyl, or $C_1$-$C_{14}$-aryl, and $R^{65}$ and $R^{66}$ together are a chemical bond; or $R^{63}$ and $R^{64}$ are independently hydrogen, or methyl, and $R^{65}$ and $R^{66}$ together are a $C_3$-$C_{10}$-alkane-1,3-diyl, $C_3$-$C_{10}$-alkane-1,4-diyl, or $C_3$-$C_{10}$-alkane-1,3-diyl bridge; or $R^{65}$ and $R^{66}$ together are a chemical bond, and $R^{63}$, and $R^{64}$, together with the carbon atoms to which they are bound, are part of a monocyclic or bicyclic aromatic ring system.

$R^{62}$, $R^{67}$ and $R^{68}$ are preferably independently $C_1$-$C_{12}$-alkyl, $C_3$-$C_{12}$-cycloalkyl, or $C_3$-$C_{14}$-aryl, wherein $C_3$-$C_{12}$-cycloalkyl and $C_3$-$C_{14}$-aryl are unsubstituted or substituted with 1, 2, 3, or 4 substituents independently selected from Cl, F, $C_1$-$C_8$-alkyl and $C_1$-$C_4$-alkoxy.

$R^{62}$, $R^{67}$ and $R^{68}$ are most preferably independently methyl, ethyl, 1-propyl, 2-propyl, 1-butyl, 2-butyl, tert-butyl, 1-(2-methyl)propyl, 2-(2-methyl)propyl, 1-pentyl, 1-(2-methyl)pentyl, 1-hexyl, 1-(2-ethyl)hexyl, 1-heptyl, 1-(2-propyl)heptyl, 1-octyl, 1-nonyl, 1-decyl, 1-undecyl, 1-dodecyl, adamantyl, cyclopentyl, methylcyclopentyl, cyclohexyl, methylcyclohexyl, cycloheptyl, cyclooctyl, norbornyl, phenyl, napthyl, tolyl, xylyl, chlorophenyl or anisyl.

The ligand may also be a bidentate or multidentate ligand that comprises one or two coordinating nitrogen atoms and an additional carbon atom that is bound to the transition metal. Preferably, a 5-membered ring is formed, when the additional carbon atom binds to the transition metal, as for example with 2-phenylpyridine or 6-phenyl-2,2'-bipyridine.

Suitable tridentate ligands are, for example, ligands of formula (IIh)

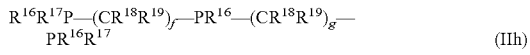

(IIh)

wherein $R^{16}$, $R^{17}$, $R^{18}$, and $R^{19}$ are each as already defined, and f and g are independently 1, 2, 3, 4, or 5, preferably 2, 3, or 4.

Exemplary tridentate ligands are ((methylphosphinediyl)bis-(methylene))bis(dimethylphosphine), ((ethylphosphindiyl)bis(methylene))bis(diethyl-phosphine), and ((methylphosphinediyl)bis(methylene))bis(diphenylphosphine).

In addition to the above-described ligands, the transition metal complex may also have at least one further ligand selected from the alkoxide, the conjugate acid of the alkoxide, halides, amines, amides, oxides, phosphides, carboxylates, acetylacetonate, aryl- or alkylsulfonates, hydride, CO, olefins, dienes, cycloolefins, nitriles, aromatics and heteroaromatics, ethers, $PF_3$, phospholes, and mono-, di- and polydentate phosphinite, phosphonite, phosphoramidite and phosphite ligands.

Any of these further ligands can be displaced when the alkene and carbon dioxide are reacted.

The transition metal complex, e.g., palladium or nickel complex, may for example be obtained from the ligand and the transition metal, e.g., palladium or nickel, or from the ligand and a transition metal source, e.g., palladium or nickel source, comprising the transition metal, e.g., palladium or nickel, at oxidation state 0. Alternatively, the transition metal complex may for example be obtained by reducing a salt of the transition metal with a reducing agent, e.g., $H_2$, Mg, Na or Zn.

Palladium sources include, for example, $PdL_2$, $PdL_4$, $LPdX_2$, $L_2PdX_2$, $L_2Pd_2X_2$, $LPd_2X_4$, $Pd_3X_6$, $L_3Pd_2$, $L_2Pd_2$, wherein X is selected from halide, pseudohalide, carboxylate, alkoxide, carbonate, sulfate, nitrate, hydroxide, acetylacetonate, cyclopentadiene, alkyl, and aryl, and L is a neutral ligand selected from phosphine, amine, olefin, carbonyl and nitrile, and the corresponding adducts with solvents such as ethers, DMSO, or water.

The palladium sources and salts are preferably selected from $[Pd_2(Allyl)_2(Cl)_2]$, $[Pd_2(Methallyl)_2(Cl)_2]$ $[Pd(dba)_2]$, $[Pd_2(dba)_3]$, $PdCl_2$, $PdBr_2$, $PdI_2$, $Pd(NO_3)_2$, $PdSO_4$ [Pd (OAc)₂], [Pd(PtBu₃)₂], [Pd(PCy₃)₂], [Pd(PoTolyl₃)₂], [Pd (PPh₃)₄], [Pd(COD)(Cl)(Me)], [Pd(Phen)(OAc)₂], [Pd₂ (PtBu₃)₂(Br)₂], [Pd(C₆H₅CN)₂(Cl)₂], [Pd(PCy₃)₂(Cl)₂], [Pd (PPh₃)₂(Cl)₂], [Pd(norbornadiene)(Cl)₂], [Pd(TMEDA) (Cl)₂], [Pd(TMEDA)(CH₃)₂], [Pd₃(OAc)₆], [Pd(CF₃ COO)₂], [Pd(Acetylactonate)₂] and [Pd(COD)(Cl)₂], [Pd (Allyl)(Cp)]. Nickel sources and salts include, for example, NiL₂, NiL₄, LNiX₂, L₂NiX₂, L₂Ni₂X₂ wherein X and L are as defined above and the corresponding adducts with solvents such as ethers, DMSO, or water.

The nickel sources and salts are preferably selected from [Ni(COD)₂], NiF₂, NiCl₂, NiBr₂, NiI₂, [Ni(OAc)₂], [Ni (Acetylactonate)₂], [Ni(Ph₃P)₂(Cl)₂], [Ni((PPh₂)₂Fc)(Cl)₂], [Ni₂(Methallyl)₂(Cl)₂], [Ni₂(allyl)₂(Cl)₂], [Ni(CO)₄], [Ni (PPh₃)₂(CO)₂], [Ni(NO₃)₂], [Ni(OH)₂], [Ni(PPh₃)₄], [Ni (CF₃COO)₂], [Ni(SO₄)], [Ni(2-ethylhexanoate)₂], [Ni(P (OPh)₃)₄], [Ni(C₇H₁₅COO)₂], [Ni(Cp)₂], [Ni(PCy₃)₂(Cl)₂], [Ni(PMe₃)₂(Cl)₂], [Ni(PBu₃)₂(Br)₂], and [Ni(dppe)(Cl)₂].

Abbreviations used in the above palladium and nickel sources and salts:
dba is dibenzylideneacetone
Cy is cyclohexyl
COD is 1,5-cyclooctadiene
Phen is phenanthroline
TMEDA is N,N,N',N'-tetramethylethylenediamine
Fc is Ferrocenyl
Cp is cyclopentadienyl Many of the above palladium and nickel sources and salts are commercially available.

Suitable alkenes are those of the following general formula

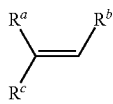

wherein
$R^a$, $R^b$ and $R^c$ are each independently hydrogen, $C_{1-12}$-alkyl, $C_{2-12}$-alkenyl, or $R^a$ and $R^b$ together with the carbon atoms to which they are bonded are a monoethylenically or diethylenically unsaturated, 5- to 8-membered carbocycle.

Suitable alkenes are, for example, ethene, propene, isobutene, butadiene, piperylene, 1-butene, 1-pentene, 1-hexene, 1-heptene, 1-octene, 1-nonene, 1-decene, 2-butene, cyclopentene, cyclohexene, cycloheptene, cyclooctene, cyclooctadiene, or styrene. The alkene to be used in the process according to the invention is generally gaseous or liquid under the reaction conditions.

A preferred alkene is ethene. The process according to the invention makes it possible to obtain an acrylate.

Alternatively, the alkene is piperylene and a sorbate is obtained.

In the carboxylation reaction, the alkene partial pressure is, for example, in the range from 0.5 bar to 200 bar, preferably from 1 bar to 100 bar, in particular from 2 bar to 80 bar, further preferred from 3 bar to 60 bar, most preferably from 5 to 50 bar.

All pressures indicated herein are absolute pressures.

The efficiency of the process according to the invention does improve further when the partial pressure of carbon dioxide is increased. The partial pressure of carbon dioxide in the carboxylation reaction is preferably in a range from 1 to 200 bar, preferably from 2 to 160 bar, in particular from 4 to 140 bar, further preferred from 6 to 120 bar, most preferably from 10 to 100 bar.

The carbon dioxide for use in the process according to the invention can be used in gaseous, liquid or supercritical form. It is also possible to use carbon dioxide-comprising gas mixtures available on the industrial scale, provided that they are substantially free of carbon monoxide.

The carbon dioxide and the alkene for use in the process according to the invention may also comprise inert gases such as nitrogen or noble gases. Advantageously, however, the content thereof is below 10 mol %, based on the total amount of carbon dioxide and alkene in the reactor.

The carbon dioxide and the alkene are generally fed into the carboxylation reaction, e.g. into step a), in a molar ratio in the range from 0.2 to 20 and preferably in the range from 1 to 10 moles of carbon dioxide per mole of ethene.

The contacting of the alkene and the carbon dioxide with the carboxylation catalyst, the alkoxide, and the organic solvent, may, for example, be achieved by contacting the alkene and the carbon dioxide with a fluid comprising the carboxylation catalyst, the alkoxide and the solvent.

The fluid may be gaseous or liquid or a mixture of both, gas and liquid. The fluid is preferably liquid. The catalyst and/or the alkoxide do not have to be fully dissolved in the fluid, e.g., in the liquid. It may contain particles of various size; it may, for example, contain at least some of the carboxylation catalyst and/or alkoxide in the form of particles.

Preferably, at least part of the alkoxide is homogeneously dissolved in the reaction medium. A skilled person knows that the specific structure of the alkoxide determines the solubility of the alkoxide (and of the corresponding alcohol) in the specific organic solvent that is used in the process according to the invention. The solubility of the alkoxide in the organic solvent may be controlled by the length and number of alkyl and cycloalkyl moieties comprised by the alkoxide.

The carboxylation reaction is preferably carried out in the presence of alkali metal or alkaline earth metal cations. Preferred alkali metal cations are $Na^+$, $Li^+$, and $K^+$. Preferred alkaline earth metal cations are $Mg^{2+}$ and $Ca^{2+}$. The cations are at least partially dissolved in the reaction medium. They may, for example, be bound to anions or be bound to some residue from which the cations are readily released in the form of cations, as for example, in lithiumaryls and lithiumalkyls. The alkali metal or alkaline earth metal cations may, for example, be added together with the alkoxide in the form of an alkali metal or alkaline earth metal salt of the alkoxide.

The alkoxide, e.g., secondary or tertiary alkoxide, is consumed stoichiometrically when the alkene and carbon dioxide are reacted to obtain the α,β-ethylenically unsaturated carboxylic acid salt. The alkoxide is protonated such that its conjugated acid, an alcohol, is obtained as a byproduct. The alkoxide can be regenerated by reacting the alcohol with an alkaline material which is capable of deprotonating the alcohol such that the alkoxide is regenerated. Accordingly, the process of the invention preferably comprises regenerating the alkoxide by adding an alkaline material.

The amount of the alkoxide, e.g., secondary or tertiary alkoxide, used in the process according to the invention is generally 5 to 95% by weight, preferably 20 to 60% by weight, and most preferably 5 to 25% by weight, based on the overall reaction medium in the reactor.

It is possible to use the alkoxide, e.g., secondary or tertiary alkoxide, in substoichiometric amounts based on the carboxylation catalyst. Even when substoichiometric amounts of alkoxide are used, it is possible to obtain excess α,β-ethylenically unsaturated carboxylic acid salt as based on the catalyst concentration, if the alkoxide is regenerated by addition of the alkaline material.

If the alkaline material is added outside of the carboxylation reactor, i.e. at low carbon dioxide partial pressure, alkaline materials that are inactivated at the conditions of the reaction between alkene and carbon dioxide, i.e. at high carbon dioxide partial pressure, may be used. These alkaline materials include alkali hydroxides, primary alkyl alkoxides, alkali metals or alkaline earth metal hydrides.

The alkaline material is for example selected from elemental alkali metal, alkali metal or alkaline earth metal hydrides, amides, phosphides, silanolates, alkyls, and aryls.

Suitable elemental alkali metals are sodium, lithium, and potassium. The preferred elemental alkali metal is sodium.

Suitable alkali metal or alkaline earth metal hydrides are, for example, lithium hydride, sodium hydride, potassium hydride, magnesium hydride, and calcium hydride.

Suitable alkali metal or alkaline earth metal amides are, for example, $LiNMe_2$, $LiNEt_2$, $LiN(iPr)_2$, $NaNMe_2$, $NaNEt_2$, $NaN(iPr)_2$, $KNMe_2$, $KNEt_2$, $KN(iPr)_2$, (Me=Methyl; Et=Ethyl; iPr=Isopropyl). The suitable amides also include silicon-containing amides such as sodium hexamethyldisilazide (NaHMDS), potassium hexamethyldisilazide (KHMDS) or lithium hexamethyldisilazide (LiHMDS).

Suitable alkali metal or alkaline earth metal phosphides are, for example, those of the formula $M^2PR^{101}_2$ in which $M^2$ is an alkali metal or an equivalent of an alkaline earth metal, and $R^{101}$ is $C_{1-12}$-alkyl or $C_{6-10}$-aryl, for example $KPPh_2$ or $NaPPh_2$ (Ph=Phenyl).

Suitable alkali metal or alkaline earth metal silanolates are, for example, those of the formula $M^2OSi(C_{1-4}\text{-Alkyl})_3$ in which $M^2$ is an alkali metal or an equivalent of an alkaline earth metal, for example $NaOSiMe_3$.

Suitable alkali metal or alkaline earth metal alkyls or aryls are, for example, lithium alkyl and lithium aryl compounds, such as methyllithium, n-butyllithium, sec-butyllithium, tert-butyllithium, phenyllithium, where the benzene ring may bear substituents at any position (e.g. $OCH_3$, $CH_2NMe_2$, $CONR_2$), cyclohexyllithium, where the cyclohexyl ring may comprise heteroatoms (e.g. O, N, S), ethyllithium, lithium pentadienyl, lithium 2-furanyl, lithium 2-thiophenyl, lithium ethynyl. Also suitable are sodium alkyl and sodium aryl compounds, such as sodium cyclopentadienyl.

The suitable alkaline earth metal alkyls and aryls include magnesium alkyl and magnesium aryl compounds (Grignard reagents) of the general formula $R^{102}MgX$, where $R^{102}$ may be one of the alkyl and aryl residues listed above for the lithium alkyl and lithium aryl compounds and X may be F, Cl, Br, I.

Suitable alkaline materials are also alkali metals, in particular sodium. The deprotonation of the alcohol is then coupled with a redox reaction. The alkali metal is oxidized to the alkali metal cation and the proton of the tertiary alcohol is reduced to hydrogen.

It may happen that part of the carboxylation catalyst is deactivated by oxidation of the active metal. The deactivation reduces the overall efficiency of the process. In this case, a reducing agent can be added. Apparently, the reducing agent reactivates the deactivated carboxylation catalyst by reduction of the oxidized active metal. Any reducing agent which is capable of reducing the deactivated carboxylation catalyst is suitable as the reducing agent. Preferable reducing agents are $H_2$, Mg, Na and Zn, or Phosphines.

Preferably, at least part of the carboxylation catalyst is homogeneously dissolved in the reaction medium, for example, in the form of complex-type compounds.

The reaction medium wherein the alkene and carbon dioxide are reacted preferably comprises 0.1 to 20000 ppm by weight, preferably 1 to 1000 ppm by weight, in particular 5 to 500 ppm by weight of the transition metal, based on the total weight of the reaction medium.

The carboxylation reaction, e.g., step a), is preferably carried out in a reactor which is suitable for gas/liquid reactions or liquid/liquid reactions at the given temperature and the given pressure. Suitable standard reactors for gas-liquid reaction systems are specified, for example, in K. D. Henkel, "Reactor Types and Their Industrial Application", in Ullmann's Encyclopedia of Industrial Chemistry 2005, Wiley VCH Verlag GmbH & Co KGaA, DOI: 10.1002/14356007.b04_087, chapter 3.3 "Reactors for gas-liquid reactions". Examples include stirred tank reactors, tubular reactors or bubble columns.

The carboxylation reaction, e.g., step a) of the process according to the invention may be performed continuously or discontinuously. It is preferably performed continuously.

When the carboxylation reaction is performed discontinuously, the ligand, the transition metal which may, for example, be in the form of the transition metal source, the alkoxide, carbon dioxide and the alkene may be given into the reactor. Preferably, gaseous carbon dioxide and gaseous alkene are passed into the reactor at the desired pressure. After the reaction has slowed down, pressure may be relieved by liberating unreacted carbon dioxide and/or alkene from the reactor.

The carboxylation reaction may, for example, be performed at total pressures in the range from 1 to 300 bar, preferably from 3 to 200 bar, in particular from 5 to 150 bar. The carboxylation reaction may, for example, be performed at temperatures in the range from 20 to 250° C., e.g., from 40 to 200° C., in particular from 50 to 190° C., preferably from 60 to 180° C., further preferably from 70 to 180° C., most preferably from 80 to 180° C. Particularly preferred are temperatures in the range from >80 to 180° C., for example from >100 to 170° C., e.g. from 105 to 170° C. It appears that the amount of carbonic acid half esters formed from alkoxides and $CO_2$ is in these temperature ranges even at high partial pressure of carbon dioxide small enough that the carboxylation reaction proceeds with the remaining alkoxide.

In order to achieve good mixing of the alkene, carbon dioxide, the carboxylation catalyst, the alkoxide, and the organic solvent, suitable apparatuses can be used. Such apparatuses may be mechanical stirrer apparatuses with one or more stirrers, with or without baffles, packed or nonpacked bubble columns, packed or nonpacked flow tubes with or without static mixers, or other useful apparatuses known to those skilled in the art for these process steps. Baffles and delay structures may be used.

There is no need of separately feeding the $CO_2$, the alkene and the alkoxide to the reaction. $CO_2$, the alkene, the alkoxide, the organic solvent and the carboxylation catalyst can be fed into the process either together or spatially separated. Such a spatial separation can be accomplished, for example in a stirred tank, in a simple manner by means of two or more separate inlets. When more than one tank is used, for example, there may be different media charges in different tanks. Separation of the addition of the $CO_2$ and alkene reactants in terms of time is also possible in the process according to the invention. Such a time separation can be accomplished, for example, in a stirred tank by staggering the charging with the reactants. When flow tubes or apparatus of a similar kind are used, such charging can be effected, for example, at different sites in the flow tube; such a variation of the addition sites is an elegant way of adding the reactants as a function of residence time.

One or more immiscible or only partly miscible liquid phases can be used. Supercritical media and ionic liquids can be used. In the carboxylation reaction, e.g., step a), conditions which promote formation of such states can be established. Phase transfer catalysis and/or surfactants can be used in the process according to the invention.

Preferably, the alkoxide is used in molar excess based on the carboxylation catalyst in the carboxylation reaction, e.g., step a). It is advantageous to use at least 10 moles of alkoxide, preferably at least 50 moles of alkoxide, for example 50 to 100000 moles of alkoxide, e.g., 100 to 50000 moles of alkoxide per mole of carboxylation catalyst in the carboxylation reaction, e.g., step a).

The further processing of the crude reaction product obtained in the carboxylation reaction, e.g., in step a), is not limited.

It is generally preferred to decompress the crude reaction product. Further processing steps, e.g., those described below, can then be carried out at lower pressure than the pressure at which the carboxylation reaction is performed, e.g., under atmospheric pressure. There is thus no need of using apparatuses that withstand high pressure in further processing steps. The crude reaction product may, for example, be decompressed into a decompression vessel. It can, for example, be decompressed to a pressure in the range from 0.01 to 20 bar, for example in the range from 0.1 to 10 bar.

During decompression, a gaseous phase is released from the crude reaction product. This gaseous phase comprises at least unconverted $CO_2$ and/or alkene, e.g., ethene.

The release of the gaseous phase cools the crude reaction product, which slows down any undesired reverse reaction with decomposition of α,β-ethylenically unsaturated carboxylic acid salt to carbon dioxide and alkene and facilitates further processing steps. Preferably, the $CO_2$ and/or alkene, e.g., ethene, comprised by the gaseous phase is recycled into the process, e.g., into step a).

The gaseous phase may further comprise alcohol byproduct if the alcohol byproduct or at least part of it is evaporated when the crude reaction product is decompressed, i.e. when a low boiling alcohol byproduct is formed. The other main constituents of the crude reaction product, i.e. the α,β-ethylenically unsaturated carboxylic acid salt, the carboxylation catalyst and also the organic solvent are less volatile. Most or all of these other main constituents do therefore remain in the liquid state, when the crude reaction product is decompressed.

The decompression can be carried out in order to selectively evaporate part of the alcohol byproduct (but not the much less volatile organic solvent) from the crude reaction product. The gaseous phase released upon decompression of the crude reaction product is preferably cooled in order to recover a condensate comprising at least some of the alcohol byproduct released with the gaseous phase. The recovery of such condensate is preferred when a volatile alcohol byproduct is comprised by the crude reaction product. The condensate is preferably recovered when the boiling temperature of the conjugate acid of the alkoxide, i.e. the boiling temperature of the alcohol byproduct at a pressure of 1 bar is at most 150° C., for example, at most 140° C., in particular at most 130° C., preferably at most 120° C., most preferably at most 110° C.

The α,β-ethylenically unsaturated carboxylic acid salt is preferably removed from the crude reaction product, e.g., from the depressurized crude reaction product.

The removal of the α,β-ethylenically unsaturated carboxylic acid salt does preferably comprise a liquid-liquid phase separation of a first liquid phase in which the α,β-ethylenically unsaturated carboxylic acid salt is enriched, and a second liquid phase in which the carboxylation catalyst is enriched.

These two phases may form in the course of the carboxylation reaction even without adding a polar solvent, in particular when the alcohol byproduct is incompletely miscible with the organic solvent.

Preferably, the process according to the invention comprises a step, wherein at least part of the crude reaction product, e.g., the decompressed crude reaction product, is contacted with a polar solvent such that a first liquid phase in which the α,β-ethylenically unsaturated carboxylic acid salt is enriched, and a second liquid phase in which the carboxylation catalyst is enriched, are obtained. This step is referred to as step b) in the following.

"Enriched" is understood to mean a partition coefficient P of each of the carboxylation catalyst, and the α,β-ethylenically unsaturated carboxylic acid salt of >1.

$$P_1 = \frac{[\text{Concentration of the carboxylation catalyst in the second liquid phase}]}{[\text{Concentration of the carboxylation catalyst in the first liquid phase}]}$$

$$P_2 = \frac{[\text{Concentration of the } \alpha, \beta\text{-ethylenically unsaturated carboxylic acid salt in the first liquid phase}]}{[\text{Concentration of the } \alpha, \beta\text{-ethylenically unsaturated carboxylic acid salt in the second liquid phase}]}$$

The partition coefficient $P_1$ is preferably ≥10 and more preferably ≥20, further preferably ≥100, most preferably ≥1000, for example ≥10000.

The partition coefficient $P_2$ is preferably ≥10 and more preferably ≥20, further preferably ≥100, most preferably ≥1000, for example ≥10000.

A rapid separation of the first liquid phase from the second liquid phase may supress a reverse reaction with decomposition to carbon dioxide and alkene. In addition, losses of active metal are low as the catalyst is retained in the second liquid phase.

Preferably, the main constituent of the second liquid phase is the organic solvent.

The carboxylation catalyst is generally selected by a simple experiment in which the partition coefficient of the desired catalyst is determined experimentally under the planned process conditions.

Any polar solvent in which the α,β-ethylenically unsaturated carboxylic acid salt has good solubility and which has zero or only limited miscibility with the second liquid phase, e.g., with the organic solvent as specified above, in which the carboxylation catalyst is enriched, is suitable. The polar solvent should be selected such that the polar solvent is present in enriched form in the first liquid phase. "Enriched" is understood to mean a proportion by weight of >50% of the polar solvent in the first liquid phase based on the total amount of polar solvent in both liquid phases. The proportion by weight is preferably >90%, more preferably >95% and most preferably >97%. The polar solvent is generally selected by simple tests in which the partition of the polar solvent in the two liquid phases is determined experimentally under the process conditions.

Substance classes which are suitable as polar solvents are water, as well as alcohols, diols and the carboxylic esters thereof, polyols and the carboxylic esters thereof, sulfones, sulfoxides, which have zero or only limited miscibility with the organic solvent, and their mixtures.

Examples of suitable alcohols are methanol, ethanol, 1-propanol, isopropanol, tert-butanol and butanol. Examples of suitable diols and polyols are ethylene glycol, diethylene glycol, triethylene glycol, polyethylene glycol, 1,3-propanediol, 2-methyl-1,3-propanediol, 1,4-butanediol, dipropylene glycol, 1,5-pentanediol, 1,6-hexanediol and glycerol.

Examples of suitable sulfoxides are dialkyl sulfoxides, preferably $C_1$- to $C_6$-dialkylsulfoxides, especially dimethyl sulfoxide.

The polar solvent is preferably selected from polar solvents that have a boiling temperature of less than 150° C. at a pressure of 1 bar.

More preferred polar solvents are aqueous phases or alcohols. Most preferably, the polar solvent comprises at least 90% by weight of water, for example, at least 95% by weight of water. The polar solvent is, for example, water.

In order to separate the liquid phases, one may, for example, conduct only the first liquid phase out of the carboxylation reactor and leave the second liquid phase within the carboxylation reactor.

Alternatively, one may conduct a liquid-liquid mixed-phase stream out of the carboxylation reactor. The liquid-liquid phase separation can then be performed in a suitable apparatus outside the carboxylation reactor.

The first and the second liquid phase are generally separated by gravimetric phase separation. Suitable examples for this purpose are standard apparatus and standard methods which can be found, for example, in E. Müller et al., "Liquid-Liquid Extraction", in Ullmann's Encyclopedia of Industrial Chemistry, 2005, Wiley-VCH Verlag GmbH & Co. KGaA,DOI:10.1002/14356007.b03_06, chapter 3 "Apparatus". In general, the first liquid phase enriched with the α,β-ethylenically unsaturated carboxylic acid salt is heavier and forms the lower phase.

Supercritical media and ionic liquids, and the establishment of conditions which promote the formation of such states, may be applied for phase separation. Preferably, the phase separation of the first and the second liquid phase is facilitated by changing temperature and/or pressure.

Liquid-liquid extraction can be effected in all apparatus suitable for this purpose, such as stirred vessels, extractors or percolators.

Step b) may be performed continuously or discontinuously. It is preferably performed continuously.

Step b) may, for example, be performed at the same or lower total pressure than step a). Step b) is preferably performed at lower total pressure than step a). Step b) is preferably performed at a total pressure in the range from 0.01 to 20 bar, for example in the range from 0.1 to 10 bar.

The alcohol byproduct can be enriched either in the first or in the second liquid phase. Its distribution depends on the solubility of the alcohol byproduct in the specific organic solvent and in the specific polar solvent. A specific combination of organic solvent and polar solvent may be chosen in order to ensure an enrichment of the alcohol byproduct in the first or in the second liquid phase.

When the alcohol byproduct is enriched in the first liquid phase, the partition coefficient $P_3$ of the alcohol byproduct of is <1. When the alcohol byproduct is enriched in the second liquid phase, the partition coefficient $P_3$ of the alcohol byproduct of is >1. $P_3$ is defined as specified below:

$$P_3 = \frac{[\text{Concentration of the alcohol byproduct in the second liquid phase}]}{[\text{Concentration of the alcohol byproduct in the first liquid phase}]}$$

In a preferred process according to the invention, at least part of the second liquid phase, e.g., of the second liquid phase obtained in step b), is recycled into the carboxylation reaction, e.g., to step a). The second liquid phase may be recycled into the carboxylation reaction with or without further workup steps. Traces of water comprised by the second liquid phase can be removed by distillation or by contacting the second liquid phase with a drying agent. When traces of water comprised by the second liquid phase are tolerated by the carboxylation reaction, the second liquid phase can be recycled to the reaction without further drying.

The preferred choice of further processing steps does depend on the distribution of the alcohol byproduct, i.e. on the concentration of the alcohol byproduct in the first and in the second liquid phase.

In a preferred process according to the invention, at least some of the alcohol byproduct formed in the carboxylation reaction is contacted with the alkaline material in order to regenerate the alkoxide and the regenerated alkoxide is recycled into the carboxylation reaction, e.g., to step a). It may, for example, be sufficient to regenerate the alkoxide from the alcohol byproduct comprised by the condensate, to regenerate the alkoxide from the alcohol byproduct comprised by the first liquid phase, or to regenerate the alkoxide from the alcohol byproduct comprised by the second liquid phase and to recycle only this regenerated alkoxide into the carboxylation reaction. If alkoxide is regenerated only from part of the alcohol byproduct that is comprised by the crude reaction product, the remaining alcohol byproduct can be recycled into the process, for example into the carboxylation reaction, e.g., to step a).

Alternatively or additionally, the reaction medium of the carboxylation reaction may be brought into contact with the alkaline material. The alkaline material may, for example, be added to the reaction medium. Alcohol byproduct can then be directly recycled into the carboxylation reaction and the alkoxide is regenerated from the alcohol byproduct in the reaction medium.

If the alcohol byproduct is enriched in the second liquid phase, alkoxide is preferably at least partially regenerated from the alcohol byproduct comprised by the second liquid phase by bringing the second liquid phase into contact with the alkaline material, e.g., by adding the alkaline material to the second liquid phase. This is particularly advantageous when a relatively high proportion of the alcohol byproduct is present in the second liquid phase, in particular if 90% or more of the alcohol byproduct comprised by the crude reaction product or by the decompressed crude reaction product is present in the second liquid phase obtained in step b). The polar solvent can be removed from the first liquid phase, preferably by distillation or evaporation, to obtain the α,β-ethylenically unsaturated carboxylic acid salt. A distillation fraction containing the polar solvent can be recycled into the process, e.g., into step b).

If the alcohol byproduct is enriched in the first liquid phase, there is in general no need of regenerating alkoxide from the alcohol byproduct comprised by the second liquid phase because there is no or only little alcohol byproduct comprised by the second liquid phase. The second liquid phase can be recycled into the carboxylation reaction, e.g., to step a), without alkoxide regeneration. Recycling of the second liquid phase without alkoxide regeneration may, for example, be advantageous when at most 45% by weight of the alcohol byproduct, preferably at most 35% by weight of the alcohol byproduct, in particular at most 25% by weight of the alcohol byproduct, most preferably at most 10% by weight of the alcohol byproduct formed in the carboxylation reaction is comprised by the second liquid phase.

The polar solvent and the alcohol byproduct can be removed from the first liquid phase, preferably by distillation or evaporation to obtain the $\alpha,\beta$-ethylenically unsaturated carboxylic acid salt. The alcohol byproduct can be recovered by distillation in a fraction containing the alcohol byproduct. Alkoxide can be regenerated by bringing the recovered alcohol byproduct into contact with the alkaline material. The regenerated alkoxide can then be recycled into the carboxylation reaction, e.g., into step a). The polar solvent can be recovered in the form of a second distillation fraction containing the polar solvent that may be recycled into the process, e.g., into step b). This procedure is exemplified in more detail in the below specific embodiment.

If significant amounts of alcohol byproduct are comprised by both liquid phases, the overall efficiency of the process may be improved further by regenerating alkoxide from the alcohol byproduct comprised by the first liquid phase and from the alcohol byproduct comprised by the second liquid phase, according to the methods specific in the two preceding paragraphs.

In this specific embodiment of the process according to the invention, the further processing may be carried out as specified in the following. This is particularly preferred if the alcohol byproduct is enriched in the first liquid phase, e.g. if $P_3<0.5$, preferably $P_3<0.1$.

In this embodiment, the process according to the invention may comprise distilling off an alcohol byproduct from the first liquid phase. This step is referred to as step c) in the following.

When an alcohol byproduct is distilled off, the alkoxide is preferably derived from an alcohol that is not decomposed when it is distilled. The decomposition temperature of the alcohol, e.g., of the conjugate acid of the alkoxide, is preferably much higher than its boiling temperature at 1 bar. The decomposition temperature of the alcohol, e.g., of the conjugate acid of the alkoxide, is preferably at least 10° C., in particular at least 20° C., for example 30° C. to 200° C. higher than its boiling temperature at 1 bar.

This difference between decomposition temperature and boiling temperature can, for example, be established by choosing the alkoxide based on the molecular weight of its conjugate acid, i.e. of the conjugate alcohol. Low molecular weight compounds tend to have low boiling temperatures. The molecular weight of the alcohol, e.g., the conjugate acid of the alkoxide is, for example, at most 200 g/mol, preferably at most 160 g/mol, in particular at most 140 g/mol, most preferably at most 120 g/mol. The molecular weight of the conjugate acid of the alkoxide is, for example, in the range from 59 to 200 g/mol, preferably in the range from 73 to 160 g/mol, in particular in the range from 73 to 140 g/mol, most preferably in the range from 73 to 120 g/mol.

In step c), the alcohol byproduct is distilled off from the first liquid phase. This provides a first distillation fraction comprising most of the alcohol byproduct, preferably at least 90%, more preferably at least 95%, in particular at least 97%, most preferably at least 99% of the alcohol byproduct comprised by the first liquid phase being fed into step c).

It is preferable to distill off both, the alcohol byproduct, and the polar solvent from the first liquid phase being fed into step c) such that the $\alpha,\beta$-ethylenically unsaturated carboxylic acid salt is obtained as a distillation residue. Accordingly, in step c) at least a part of the polar solvent is distilled off from the first liquid phase. This yields a second distillation fraction comprising most of the polar solvent, preferably at least 90%, more preferably at least 95%, in particular at least 97%, most preferably at least 99% of the polar solvent comprised by the first liquid phase being fed into step c).

Step c) may, for example, be carried out in a distillation unit comprising a distillation column which may comprise trays or packing material. The first liquid phase is fed into the distillation unit, where it is heated and/or exposed to reduced pressure. The first and the second distillation fraction have different boiling temperatures and are released from the distillation column at different levels.

The pressure in step c) is, for example, in the range from 0.0001 to 10 bar, preferably in the range from 0.001 to 5 bar, most preferably in the range from 0.01 to 2 bar. The temperature in the bottom of the distillation column is preferably kept well above the boiling temperature of the alcohol byproduct at the distillation pressure, and, if the polar solvent is also distilled of, also well above the boiling temperature of the polar solvent at the distillation pressure. The temperature in the bottom of the distillation column is, for example, in the range from 60 to 200° C., preferably in the range from 80 to 180° C.

Step c) may be performed continuously or discontinuously. It is preferably performed continuously.

The polar solvent recovered in step c) is preferably used as the polar solvent in step b). The second distillation fraction, i.e. the distillation fraction comprising most of the polar solvent, may, for example be used as the polar solvent in step b) without further workup of the second distillation fraction.

In this embodiment, the process according to the invention preferably comprises a step wherein at least part of the alcohol byproduct recovered in step c) is contacted with an alkaline material in order to regenerate the alkoxide. This step is referred to as step d) in the following. In step d), the alkoxide is regenerated by reacting the alcohol byproduct with an alkaline material which is capable of deprotonating the alcohol byproduct such that the alkoxide is regenerated.

According to step c) the alcohol byproduct is comprised by a distillation fraction that is obtained outside of the carboxylation reactor. It can therefore be contacted with the alkaline material outside of the carboxylation reactor, i.e. at low carbon dioxide partial pressure. Nucleophilic alkaline materials that are inactivated at the conditions of the reaction between alkene and carbon dioxide, i.e. at high carbon dioxide partial pressure, may thus be used for regenerating the alkoxide. This is advantageous as some of these alkaline materials, for example, sodium hydroxide, are less costly than other less nucleophilic alkaline materials.

The alkaline material used in step d) is preferably selected from alkali metals or alkaline earth metals, alkali metal and alkaline earth metal oxides and alkali metal and alkaline earth metal hydroxides and their mixtures, in particular from Li, Na, K, Ca, $Li_2O$, $Na_2O$, $K_2O$, CaO, LiOH, NaOH, KOH, $Ca(OH)_2$, and their mixtures. Sodium hydroxide is the most preferred alkaline material used in step d).

The regeneration of the alkoxide is preferably performed in the liquid or supercritical phase at pressures in the range from 0.0001 to 150 bar, preferably from 0.001 to 100 bar, more preferably from 0.001 to 60 bar. The temperature may, for example, be in the range from −20 and 300° C., preferably from 20 to 250° C., more preferably from 40 to 200° C.

Preferably, water is removed in step d), in particular when the alkaline material is selected from alkali or alkaline earth metal oxides and hydroxides. The removal of water is, for example, achieved by evaporating the water, e.g., by distillation. Step d) is then preferably carried out in a second distillation unit. When an alkali metal or alkaline earth metal hydroxide is used as alkaline material, the regeneration of the alkoxide requires a continuous removal of the water that is formed as a byproduct. The continuous removal of the water being formed as a byproduct is achieved, e.g., by evaporating or distilling off water, for example, by azeotropic distillation of the water, e.g., with benzene, toluene, or the alcohol byproduct itself, as described, for example, in chapter 4.2 of Falbe, J., Bahrmann, H., Lipps, W., Mayer, D. and Frey, G. D. 2013, Ullmann's Encyclopedia of Industrial Chemistry, DOI: 10.1002/14356007.a01_279, or in DE 968 903.

Step d) may be performed continuously or discontinuously. It is preferably performed continuously.

Preferably, at least part of the regenerated alkoxide obtained in step d) is recycled into the carboxylation reaction, e.g., into step a). The regenerated alkoxide obtained in step d) may, for example, be recycled into the carboxylation reaction, e.g., to step a), in the form of a solution.

The invention will be described in more detail by the following examples.

In the examples, the following abbreviations are used:
DBF Dibutylformamide
Dcpe 1,2-Bis(dicyclohexyl)phosphinoethan
DMAc Dimethylacetamide
DMI 1,3-Diemthyl-2-imidalolidinone,
CHP N-Cyclohexylpyrrolidon
Cy cyclohexyl
NaOCy Sodium cyclohexyloxide
NaOiPr Sodium 2-propoxide
NaOsecBu Sodium 2-butoxide
NaOtBu Sodium tert-butoxide
NaOtPentoxide Sodium tert-pentoxide
NDP N-Dodecylpyrrolidon
NEP N-Ethylpyrrolidon
NMP N-Methylpyrrolidon
THF tetrahydrofuran
TON turnover number with respect to transition metal; mole of α,β-ethylenically unsaturated carboxylic acid salt obtained per mole of transition metal
[Pd(dcpe)(NaAcr)]

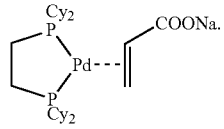

EXAMPLES 1 TO 13 (TABLE 1)

A 60 mL steel autoclave, inside a glovebox was charged with a transition metal source, ligand, and alkoxide and the obtained solid mixture was dissolved in a solvent. The autoclave was removed from the glovebox and charged, under stirring at 800 rpm, with the given pressure of ethylene and the given pressure of $CO_2$ for 15 min each at 25° C. After stirring at the given temperature for the given time at 800 rpm, the autoclave was cooled to 20° C., the pressure was released and the reaction mixture, i.e. crude reaction product, was transferred into a 100 mL glass bottle. The residues in the autoclave vessel were recovered with 15 mL of $D_2O$ and transferred in the glass bottle. To this biphasic mixture, 3-(trimethylsilyl)propionic-2,2,3,3-$d_4$ acid sodium salt (0.13 mmol, 0.0216 g), an additional 10 mL of $D_2O$, and 40 mL of $Et_2O$ were added. The organic phase, i.e. the second liquid phase, contains the carboxylation catalyst and can be recycled. From the aqueous phase, i.e. the first liquid phase, an aliquot was collected, centrifuged and analyzed by $^1$H-NMR to determine the TON. Each $^1$H-NMR spectrum showed that the aqueous phase contains the α,β-ethylenically unsaturated carboxylic acid salt (sodium acrylate), the alcohol byproduct and water. All volatiles were removed in vacuo from the aqueous phase to obtain the desired sodium acrylate as the residue. The residue was dissolved in $D_2O$ and a second $^1$H-NMR spectrum was detected. The resonances of the methyl protons of the alcohols were not present in any second $^1$H-NMR spectrum, which shows that the iso-propanol or tertiary butanol byproduct was quantitatively removed when the aqueous solvent was evaporated.

EXAMPLES 14 TO 19 (TABLE 2)

A 60 mL steel autoclave, inside a glovebox was charged with a transition metal source, ligand, and alkoxide and the obtained solid mixture was dissolved in a solvent. The autoclave was removed from the glovebox and charged, under stirring at 700 rpm, with the given pressure of ethylene and the given pressure of CO2 for 15 min each at 25° C. After stirring at the given temperature for the given time at 700 rpm, the autoclave was cooled to 20° C., the pressure was released and the reaction mixture, i.e. crude reaction product, was transferred into a 100 mL glass bottle. The residues in the autoclave vessel were recovered with 30 mL of H2O and transferred in the glass bottle. From the aqueous phase, i.e. the first liquid phase, an aliquot was collected, acidified with H3PO4 and analyzed by HPLC to determine the TON. The HPLC chromatogram showed that the aqueous phase contained the acetic acid which is the acid formed by acidifying the carboxylation product (acrylate salt).

EXAMPLES 20 TO 24 (TABLE 3)

A 100 mL Schlenk inside a glovebox was charged with Pd(PPh3)4, ligand, alkoxide, and solvent. The mixture was stirred at room temperature for 1 hour. Then, the mixture was transferred with argon to a 300 mL steel autoclave. The mixture was stirring at 700 rpm and charged with 10 bar of ethylene for 15 min at 25° C. and then with 35 bar of CO2 for 15 min at 25° C. (45 bar total pressure at 25° C.). After stirring for 16 hours at 145° C. (70-80 bar at 145° C.) the autoclave was cooled down to 20° C., the pressure was released, and the reaction mixture, i.e. the crude reaction product, was transferred into a 100 mL glass bottle. The residues in the autoclave vessel were recovered with 30 mL of $H_2O$ and transferred in a glass bottle. The aqueous phase containing the product was separated from the organic phase which contains the carboxylation catalyst that can be recycled. From the aqueous phase, an aliquot was collected (1 mL), acidified with $H_3PO_4$, and the generated acrylic acid analyzed by HPLC. The TON was determined from the HPLC analytics.

TABLE 1

| Example | Transition metal source (mmol) | Alkoxide (mmol) | Ligand (mmol) | Ethene [bar] | $CO_2$ [bar] | Solvent (mL) | Time [h] | Temperature [° C.] | TON |
|---|---|---|---|---|---|---|---|---|---|
| 1 | [Pd(dcpe)(NaAcr)] (0.1) | NaOtBu (20) | Dcpe (0.11) | 10 | 40 | DMAc (30) | 20 | 145 | 55 |
| 2 | [Pd(dcpe)(NaAcr)] (0.1) | NaOtBu (20) | Dcpe (0.11) | 10 | 40 | NMP (30) | 20 | 145 | 55 |
| 3 | [Pd(dcpe)(NaAcr)] (0.1) | NaOtBu (20) | Dcpe (0.11) | 10 | 40 | DMI (30) | 20 | 145 | 80 |
| 4 | [Pd(dcpe)(NaAcr)] (0.1) | NaOtBu (20) | Dcpe (0.11) | 10 | 40 | NEP (30) | 20 | 145 | 60 |
| 5 | [Pd(dcpe)(NaAcr)] (0.1) | NaOtBu (20) | Dcpe (0.11) | 10 | 40 | DBF (30) | 20 | 145 | 51 |
| 6 | [Pd(dcpe)(NaAcr)] (0.1) | NaOtBu (20) | Dcpe (0.11) | 10 | 40 | CHP (30) | 20 | 145 | 152 |
| 7 | [Pd(PPh$_3$)$_4$] (0.01) | NaOtBu (25) | Dcpe (0.011) | 10 | 40 | CHP (30) | 5 | 145 | 422 |
| 8 | [Pd(PPh$_3$)$_4$] (0.01) | NaOiPr (25) | Dcpe (0.011) | 10 | 40 | CHP (30) | 20 | 145 | 200 |
| 9 | [Pd(PPh$_3$)$_4$] (0.2) | NaOtBu (15) | Dcpe (0.22) | 10 | 40 | DBF (30) | 20 | 145 | 130 |
| 10 | [Pd(PPh$_3$)$_4$] (0.2) | NaOiPr (15) | Dcpe (0.22) | 10 | 40 | DBF (30) | 20 | 145 | 30 |
| 11 | [Pd(PPh$_3$)$_4$] (0.01) | NaOtBu (25) | Dcpe (0.011) | 10 | 40 | CHP (30) | 20 | 145 | 514 |
| 12 | [Pd(PPh$_3$)$_4$] (0.01) | NaOtBu (25) | Dcpe (0.011) | 10 | 40 | DBF (30) | 106 | 145 | 270 |
| 13 | [Pd(PPh$_3$)$_4$] (0.2) | NaOtBu (25) | Dcpe (0.22) | 10 | 40 | DBF (30) | 20 | 145 | 130 |

TABLE 2

| Example | Transition metal source (mmol) | Alkoxide (mmol) | Ligand (mmol) | Ethene [bar] | $CO_2$ [bar] | Solvent (mL) | Time [h] | Temperature [° C.] | TON |
|---|---|---|---|---|---|---|---|---|---|
| 14 | [Ni(COD)$_2$] (0.1) | NaOtBu (4.6) | Dcpe (0.11) | 10 | 30 | DBF (30) | 16 | 145 | 26 |
| 15 | [Ni(COD)$_2$] (0.2) | NaOtBu (20) | Dcpe (0.22) | 10 | 30 | Dimethyl-hexanamide (30) | 16 | 145 | 23 |
| 16 | [Ni(COD)$_2$] (0.1) | NaOsecBu (4.6) | Dcpe (0.11) | 10 | 30 | DBF (30) | 16 | 145 | 12 |
| 17 | [Ni(COD)$_2$] (0.1) | NaOiPr (4.6) | Dcpe (0.11) | 10 | 30 | DBF (30) | 16 | 145 | 29 |
| 18 | [Ni(COD)$_2$] (0.1) | NaOCy (4.6) | Dcpe (0.11) | 10 | 30 | DBF (30) | 16 | 145 | 17 |
| 19 | [Ni(COD)$_2$] (0.1) | NaOtPentoxide (4.6) | Dcpe (0.11) | 10 | 30 | DBF (30) | 16 | 145 | 3 |

TABLE 3

| Example | Transition metal source (mmol) | Alkoxide (mmol) | Ligand (mmol) | Ethene [bar] | $CO_2$ [bar] | Solvent (mL) | Time [h] | Temperature [° C.] | TON |
|---|---|---|---|---|---|---|---|---|---|
| 20 | [Pd(PPh$_3$)$_4$] (0.2) | NaOsecBu (20) | Dcpe (0.22) | 10 | 35 | DBF (30) | 16 | 145 | 21 |
| 21 | [Pd(PPh$_3$)$_4$] (0.2) | NaO(2-pentyl) (20) | Dcpe (0.22) | 10 | 35 | DBF (30) | 16 | 145 | 31 |
| 22 | [Pd(PPh$_3$)$_4$] (0.2) | NaO(3-methyl-2-butyl)) (20) | Dcpe (0.22) | 10 | 35 | DBF (30) | 16 | 145 | 65 |
| 23 | [Pd(PPh$_3$)$_4$] (0.2) | NaO(2,4-Bismethyl-3-pentyl) (20) | Dcpe (0.22) | 10 | 35 | DBF (30) | 16 | 145 | 46 |
| 24 | [Pd(PPh$_3$)$_4$] (0.2) | NaOtBu (20) | Dcpe (0.22) | 10 | 35 | N,N-Diisobutyl-formamide (30) | 16 | 145 | 99 |

The invention claimed is:

1. A catalytic process, suitable for preparing an α,β-ethylenically unsaturated carboxylic acid salt, the process comprising contacting an alkene and carbon dioxide with a carboxylation catalyst to obtain an α,β-ethylenically unsaturated carboxylic acid salt, wherein the carboxylation catalyst comprises a nickel or palladium complex, an alkoxide, and an organic solvent, wherein the organic solvent is incompletely miscible with water at a pressure of 1 bar at at least one temperature T and is selected from the group consisting of an amide and a urea, T being a temperature in a range from 10° C. to 90° C. wherein the amide or the urea is linear or cyclic and comprises at least 5 carbon atoms and no nitrogen bound hydrogen atoms and wherein all of the at least 5 carbon atoms other than the carbonyl carbon atom are saturated.

2. The catalytic process according to claim 1, wherein the organic solvent is an N,N-disubstituted formamide, an N,N-disubstituted acetamide, an N-substituted 2-pyrrolidone, or a 1,3-disubstituted 2-imidazolidinone.

3. The catalytic process according to claim 2, wherein the organic solvent is selected from the group consisting of N-Methylpyrrolidone, N-Ethylpyrrolidone, 1,3-Dimethyl-2-imidazolidinone, N-Cyclohexylpyrrolidone, N,N-Dibutyl-formamide, N,N-Dihexylformamide, N,N-Dibutylacetamide, N,N-Dihexylacetamide, N-Cyclohexylpyrollidone, and N-Decylpyrollidone.

4. The catalytic process according to claim 1, wherein the alkoxide comprises a secondary or tertiary carbon atom directly bound to an [O$^-$]group.

5. The catalytic process according to claim 1, wherein the alkoxide is selected from the group consisting of an alkali metal alkoxide and an alkaline earth metal alkoxide.

6. The catalytic process according to claim 1, wherein the alkene and the carbon dioxide are contacted with the carboxylation catalyst, the alkoxide, and the organic solvent at a temperature in a range from 105 to 170° C.

7. The catalytic process according to claim 1, wherein the nickel or palladium complex comprises a bidentate P,X ligand, wherein X is selected from the group consisting of P, N, O, and carbene, and P and X are separated by a bivalent linker that comprises 2 to 4 bridging atoms.

8. The catalytic process according to claim 1, wherein the alkene is ethene and the α,β-ethylenically unsaturated carboxylic acid is acrylic acid.

9. The catalytic process according to claim 1, additionally comprising
- contacting at least part of a crude reaction product with a polar solvent to obtain:
- a first liquid phase in which the α,β-ethylenically unsaturated carboxylic acid salt is enriched, and
- a second liquid phase in which the carboxylation catalyst is enriched.

10. The catalytic process according to claim 9, additionally comprising
- distilling off an alcohol byproduct from the first liquid phase, to obtain a recovered alcohol byproduct, contacting at least part of the recovered alcohol byproduct with an alkaline material to obtain a regenerated alkoxide, and
- recycling at least part of the regenerated alkoxide into the catalytic process.

11. The catalytic process according to claim 10, wherein the polar solvent has a boiling temperature of less than 150° C. at a pressure of 1 bar.

12. The catalytic process according to claim 11, wherein the polar solvent is aqueous.

13. The catalytic process according to claim 12, wherein at least a part of the polar solvent is distilled off from the first liquid phase.

\* \* \* \* \*

UNITED STATES PATENT AND TRADEMARK OFFICE
CERTIFICATE OF CORRECTION

PATENT NO. : 10,774,024 B2
APPLICATION NO. : 16/090731
DATED : September 15, 2020
INVENTOR(S) : Schaub et al.

Page 1 of 2

It is certified that error appears in the above-identified patent and that said Letters Patent is hereby corrected as shown below:

On the Title Page

In Column 2, Item (57), under "ABSTRACT", Line 8, delete "at" (first occurrence).

In the Specification

In Column 1, Line 35, delete "CO2" and insert -- $CO_2$ --.

In Column 3, Line 29, delete "at" (first occurrence).

In Column 3, Line 33, delete "at" (first occurrence).

In Column 3, Line 42, delete "at".

In Column 4, Line 54, delete "at".

In Column 4, Line 61, delete "one".

In Column 5, Line 6, delete "at".

In Column 7, Line 2, delete ""O-((1-methyl)-cyclohexl)." and insert -- $^-$O-((1-methyl)-cyclohexyl). --, therefor.

In Column 7, Line 28, insert -- is -- after "catalyst".

In Column 9, Line 3, delete "napthyl," and insert -- naphthyl, --.

In Column 14, Line 15, delete "napthyl," and insert -- naphthyl, --.

In Column 25, Line 46, delete "N-Dodecylpyrrolidon" and insert -- N-Dodecylpyrrolidone --.

Signed and Sealed this
Nineteenth Day of October, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,774,024 B2

In Column 26, Line 34, delete "CO2" and insert -- $CO_2$ --.

In Column 26, Line 40, delete "H2O" and insert -- $H_2O$ --.

In Column 26, Line 42, delete "H3PO4" and insert -- $H_3PO_4$ --.

In Column 26, Line 50, delete "Pd(PPh3)4," and insert -- $Pd(PPh_3)_4$, --.

In Column 26, Line 54, delete "CO2" and insert -- $CO_2$ --.

In the Claims

In Column 27, Claim 1, Line 56, delete "at" (first occurrence).

In Column 27, Claim 1, Line 59, delete "C." and insert -- C., --.